United States Patent
Barre et al.

(10) Patent No.: US 7,230,123 B2
(45) Date of Patent: Jun. 12, 2007

(54) UREIDO OR CARBAMATE DERIVATIVES OF CROWN ETHERS AND OF SILICON USABLE FOR PREPARING SUPPORTS INTENDED FOR THE SEPARATION BY CHROMATOGRAPHY OF METAL CATIONS AND OF ORGANIC MOLECULES COMPRISING AMINE FUNCTIONAL GROUPS

(75) Inventors: Yves Barre, Uchaux (FR); Marc Simon, Orange (FR); Roger Neige, Pierrelatte (FR); Raphaël Duval, Deauville (FR)

(73) Assignee: Commissariat a l'Energir Atomique, Paris (FR)

( * ) Notice: Subject to any disclaimer, the term of this patent is extended or adjusted under 35 U.S.C. 154(b) by 117 days.

(21) Appl. No.: 10/502,120

(22) PCT Filed: Jan. 20, 2003

(86) PCT No.: PCT/FR03/00168

§ 371 (c)(1),
(2), (4) Date: Jul. 16, 2004

(87) PCT Pub. No.: WO03/062250

PCT Pub. Date: Jan. 31, 2003

(65) Prior Publication Data

US 2005/0143587 A1 Jun. 30, 2005

(30) Foreign Application Priority Data

Jan. 23, 2002 (FR) .................................. 02 00804

(51) Int. Cl.
C07D 323/00 (2006.01)
(52) U.S. Cl. .................................... 549/214
(58) Field of Classification Search ................ 549/214
See application file for complete search history.

(56) References Cited

U.S. PATENT DOCUMENTS 4,518,758 A   5/1985   Cavezzan et al.

OTHER PUBLICATIONS

Nakajima et al., Ion-chromatographic Behavior of Silica Gels Modified by Poly- and Bis(crown ether)s of Benzo-18-crown-6, Bull. Chem. Soc. Japan, vol. 56, No. 10, pp. 3052-3056 (1983).*
IUPAC Compendium of Chemical Terminology, The Gold Book, 2nd Ed. (1997).*
Nakajima et al., Ion-chromatographic Behavior of Silica Gels Modified by Poly- and Bis(crown ether)s of Benzo-18-crown-6, Bull. Chem. Soc. Japan, vol. 56, No. 10, pp. 3052-3056 (1983).*
D'Acquarica, I et al., "Application of a new chiral stational phase containing the glycopeptide antibiotic A-40, 926, in the direct chromatographic resolution of beta-amino acids", Tetrahedron: Asymmetry, vol. 11, 2000, pp. 2375-2385.

D'Acquarica, I et al., "Direct chromatographic resolution of carnitine and o-acylcarnitine enantiomers on a teicoplanin-bonded chiral stationary phase", Journal of Chromatography A, vol. 857, No. 1-2, 1999, pp. 145-155.
Dotsevi, G. et al., "Chromatographic optical resolution through chiral complexation of amino ester salts by a host covalently bound to silica gel", J. Am. Chem. Soc., vol. 97, No. 5, 1975, pp. 1259-1261.
Favre-Reguillon, A. et al., "Synthesis and evaluation of new polyurethans-based material for ion separation", Tetrahedron Letters, vol. 36, No. 36, 1995, pp. 6439-6442.
Favre-Reguillon, A. et al. "Polymeric and immobized crown compounds, material for ion separation", Tetrahedron, vol. 53, No. 4, 1997 pp. 1343-1360.
Hankins, M. G. et al., "Immobilization of crown ether carboxylic acids on silica gel and their use in column concentration of alkali metal cations from dilute aqueous solutions", Anal. Chem., vol. 68, No. 17, 1996, pp. 2811-2817.
Hyun, M. H. et al., "Liquid chromatographic resolution of racemic amines and amino alcohols on a chiral stationary phase derived from crown ether", Journal of Chromatography, vol. 837, No. 1-2, 1999 pp. 75-82.
Hyun, Myung H. et al., "Liquid chromatographic resolution of racemic amino acids and their derivatives on a new chiral stationary phase based on crown ether", Journal of Chromatography, vol. 822, No. 1, 1998, pp. 155-161.
Iwachido, T. et al., "The chromatographic behavior of alkali and alkaline earth metal cations on crown ether-modified silica gels and polymer matrices", Bull. Chem. Soc. Jpn, vol. 59, 1986, pp. 1475-1480.
Könotos, Z. et al. ,"Enantioseparation of racemic organic ammonium perchlorates by a silica gel bound optically active di-tert-butylpyridino-18-crown-6 ligand", Tetrahedron: Asymmetry, vol. 10, No. 11, 1999, pp. 2087-2099.
Lauth et al., "Ion chromatographic separation on silica grafted with benzo-18-c-6 crown ether" journal of liquid chromography", vol. 8, No. 13, 1985, pp. 2403-2415.

(Continued)

*Primary Examiner*—Joseph K. McKane
*Assistant Examiner*—Andrew B. Freistein
(74) *Attorney, Agent, or Firm*—Hutchison Law Group PLLC

(57) ABSTRACT

The invention relates to ureido or carbamate derivatives of crown ethers and of silicon of formula:

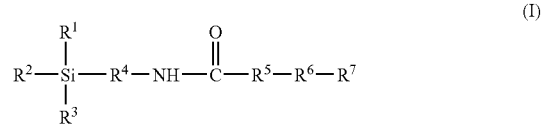

(I)

These derivatives can be grafted to silica gel for the purpose of obtaining supports for the chromatographic separation of cations or of molecules comprising amine functional groups, such as amino acids.

10 Claims, 3 Drawing Sheets

OTHER PUBLICATIONS

Machida et al., "Enantiomer separation of amino compounds by novel chiral stationary phase derived from crown ether", Journal of Chromatography A, vol. 805, 1998, pp. 85-92.

Machida et al., "Nuclear magnetic resonance studies for the chiral recognition of the novel chiral stationary phase derived from 18-crown-6 tetracarboxylic acid", Journal of Chromatography A., 1998, pp. 33-41, vol. 810, No. 1-2.

March, J, "Advanced Organic Chemistry", 4th Edition, 1992, pp. 891-903, John Wiley & Sons, NY.

Nakajima, et al., "Ion chromatography on poly(crown ether) —modified silica possessing high affinity for sodium", Journal of Liquid Chromatography", vol. 7, No. 11, 1984, pp. 2115-2125.

Nakajima, M. et al., "Ion-chromatographic behavior of silica gels modified by poly- and bis(crown ether)s of benzo-18-crown-6", Bull. Chem. Soc. Jpn., vol. 56, No. 10, 1983, pp. 3052-3056.

Nakajima, M. et al., "Liquid chromatography of alkali and alkaline earth metal salts on poly(benzo-15-crown-5)- and bis(benzo-15-crown-5)-modified silicas", Anal. Chem, vol. 55, 1983, pp. 463-467.

Rosini, C. et al., "Cinchona alkaloids for preparing new, easily accessibnle chiral stationsary phases. I.11-(10, 11-dihydro-6'-methoxy-cinchonan-9-ol) tiopropyisitanized silica", Tetrahedron Letters, vol. 26, No. 28, 1985 pp. 3361-3364.

Rosset, R. et al., "Cromatographies en phases liquide et supercritique", 3rd Edition, 1991 Masson, Paris Cedex, France pp. 290-299.

Scott, Raymond, "Silica gel and bonded phases —their production, properties and use in IC", John Wiley & Sons, 1993, pp. 140-175.

Stuurman, H. W. et al., "HPLC-Separation of enantiomers using quinine, covalently bonded to silica as stationary phase", Chromatographia, vol. 25, No. 4, 1988, pp. 265-271.

Tambute, A. et al., "design and synthesis of chiral stationary phases derived from (s)-n-(3,5-dinitrobenzoyl) tyrosine for the chromatograohuc resolution of enantiomers", New J. Chem. vol. 13, 1989, pp. 625-637.

* cited by examiner

UREIDO OR CARBAMATE DERIVATIVES OF CROWN ETHERS AND OF SILICON USABLE FOR PREPARING SUPPORTS INTENDED FOR THE SEPARATION BY CHROMATOGRAPHY OF METAL CATIONS AND OF ORGANIC MOLECULES COMPRISING AMINE FUNCTIONAL GROUPS

This is a National filing under 35 U.S.C. § 371 of PCT/FR03/00168, filed Jan. 20, 2003.

TECHNICAL FIELD

A subject-matter of the present invention is novel ureido or carbamate derivatives of crown ethers and of silicon which can be used for preparing supports intended for the separation by chromatography of cations and of molecules comprising amine functional groups, such as amino acids. It relates more particularly to supports based on silica gel to which crown ether ureido or carbamate groups are grafted.

STATE OF THE ART

The grafting of groups comprising a crown ether to silica gels had already been envisaged, as is described in J. Am. Chem. Soc., 97, 1975, p. 1259–1261 [1]; Anal. Chem., 55, 1983, p. 463–467 [2]; Bull. Chem. Soc. Jpn, 56, 1983, p. 3052–3056 [3]; Bull. Chem. Soc. Jpn, 59, 1986, p. 1475–1480 [4] and Anal. Chem., 68, 1996, p. 2811–2817 [5].

However, the synthetic routes used are complex and use arms for connecting the crown ether to the silica gel comprising neither ureido group nor carbamate group.

Furthermore, these syntheses do not make it possible to obtain a high density of groups grafted to the silica gel.

Account of the Invention

According to the invention, it has been found that ureido or carbamate derivatives of crown ether and of silicon make it possible to obtain supports based on a silica gel having a high density of crown ether groups per g of support.

Consequently, a subject-matter of the invention is novel compounds which are ureido or carbamate derivatives of crown ether and of silicon which can be used for the manufacture of such supports.

According to the invention, the compound corresponds to the formula (I):

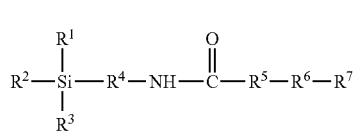

in which:

$R^1$, $R^2$ and $R^3$, which can be identical or different, represent a halogen atom or an alkoxy group of 1 or 2 carbon atoms;

$R^4$ represents a substituted or unsubstituted hydrocarbonaceous group of 1 to 20 carbon atoms optionally comprising, in its chain, one or more heteroatoms chosen from S, O, N and Si;

$R^5$ represents —NH— or —O—;

$R^6$ represents a single bond or a substituted or unsubstituted hydrocarbonaceous group of 1 to 20 carbon atoms optionally comprising, in its chain, one or more heteroatoms chosen from S, O, N and Si; and $R^7$ represents a group derived from a crown ether.

These compounds comprise a trifunctional silane group which makes it possible to carry out the grafting of the compound to the silica gel.

Preferably, the $R^1$, $R^2$ and $R^3$ groups of the trifunctional silane are methoxy or ethoxy groups. However, it is possible to use a trifunctional silane in which $R^1$, $R^2$ and $R^3$ are halogen atoms (fluorine, chlorine, bromine, iodine), preferably chlorine.

In these compounds, $R^4$ and $R^6$ independently represent a substituted or unsubstituted, aliphatic, cycloaliphatic or aromatic hydrocarbonaceous group optionally comprising one or more heteroatoms chosen from O, S, N and Si. $R^6$ can also represent a single bond.

Thus, $R^4$ and $R^6$ can be an alkylene group, for example of formula —$(CH_2)_n$— with n being an integer from 1 to 20; an arylene group, for example a phenylene group; an alkylarylene group, for example a para-xylene group; an arylalkylene group; and groups comprising a sequence of alkylene and arylene groups optionally connected by O, S, N and/or Si atoms.

Mention may be made, as example of such a sequence, of the group of formula (II):

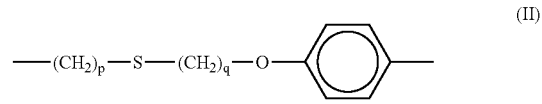

in which p and q are identical or different integers such that $p+q \leq 14$.

In the compounds of formula (I), $R^5$ can represent —NH—, which corresponds to the ureido derivatives, or —O—, which corresponds to the carbamate derivatives.

According to the invention, the $R^7$ group is derived from a crown ether, such as those corresponding to the following formulae:

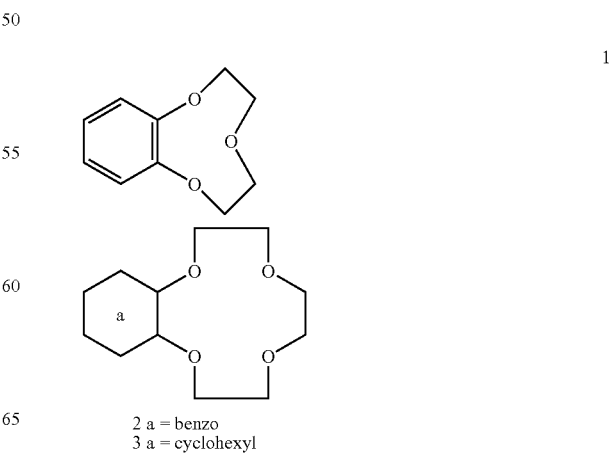

2 a = benzo
3 a = cyclohexyl

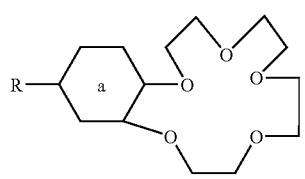
4 a = benzo R = H
5 a = benzo R = r-butyl
6 a = 2,3-naphtho
7 a = cyclohexyl R = H
8 a = cyclohexyl R = t-butyl
9 a = decalyl
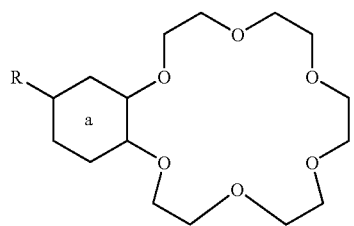
10 a = benzo R = H
11 a = benzo R = t-butyl
12 a = 2,3-naphtho
13 a = cyclohexyl R = H
14 a = cyclohexyl R = t-butyl
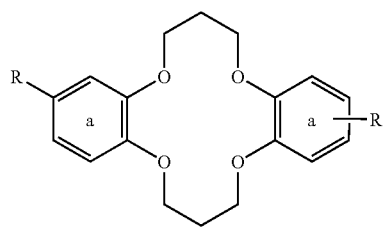
15 a = benzo R = H
16 a = benzo R = t-butyl
17 a = cyclohexyl R = H
18 a = cyclohexyl R = t-butyl
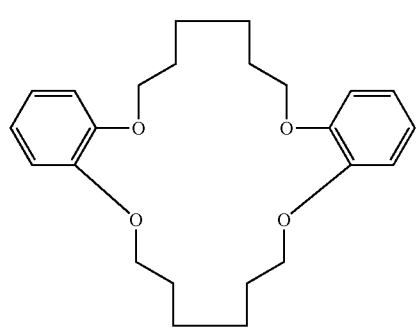
19
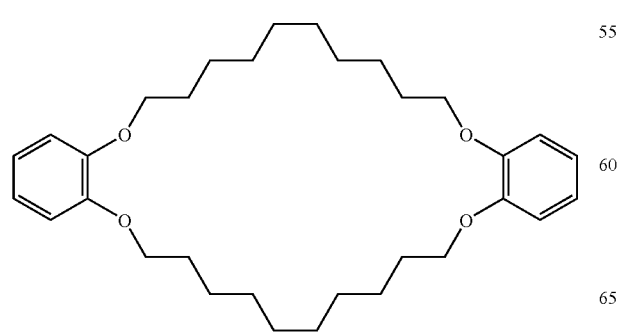
20
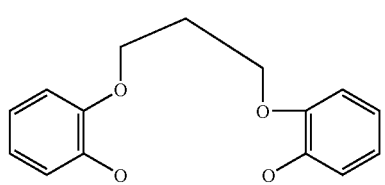
21
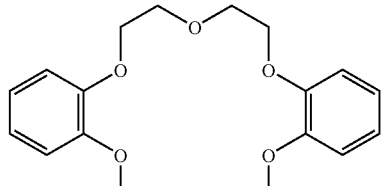
22
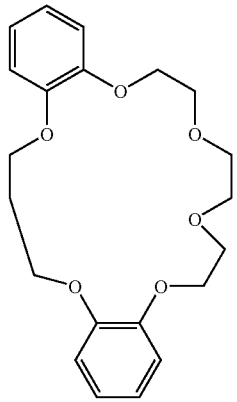
23
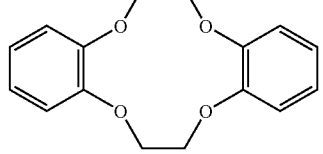
24
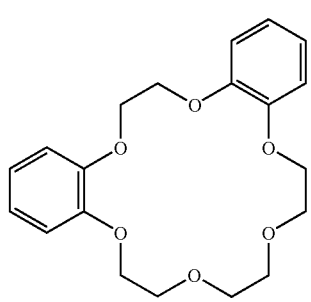
25
26

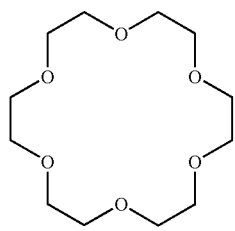
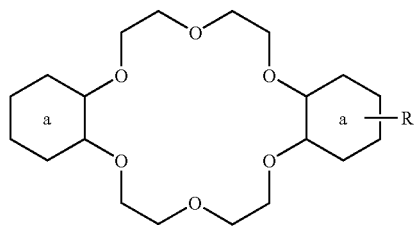
28 a = benzo R = H
29 a = benzo R = t-butyl
30 a = 2,3-naphtho
31 a = cyclohexyl R = H
32 a = cyclohexyl R = t-butyl
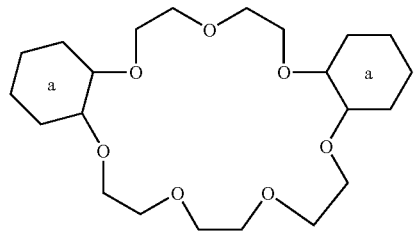
33 a = benzo
34 a = cyclohexyl
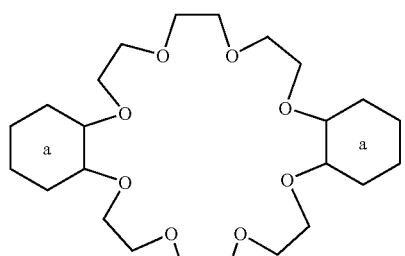
35 a = benzo
36 a = cyclohexyl
37 a = 2,3-naphtho
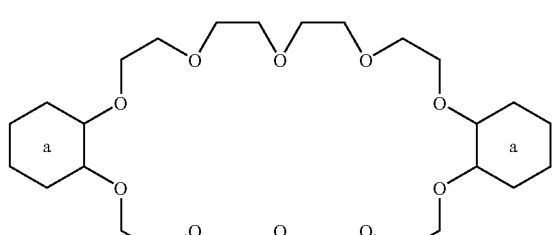
38 a = benzo
39 a = cyclohexyl
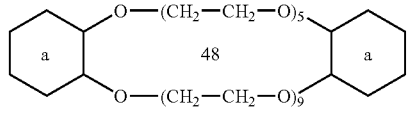
40 a = benzo
41 a = cyclohexyl
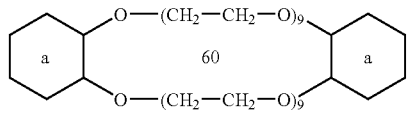
42 a = benzo
43 a = cyclohexyl
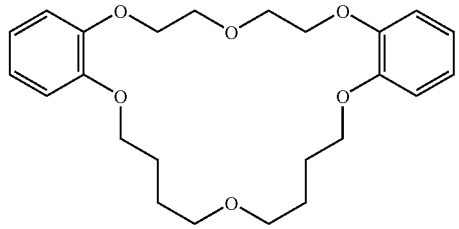
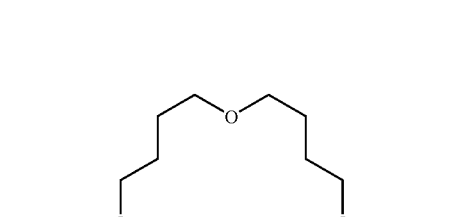
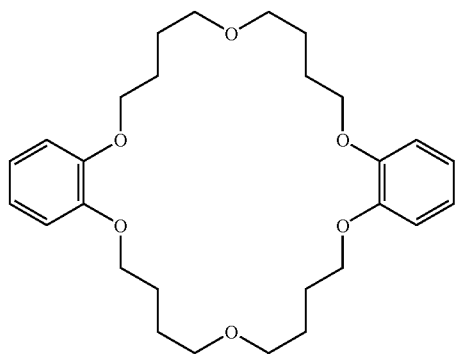

-continued

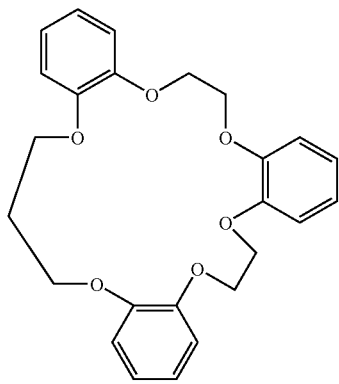
47

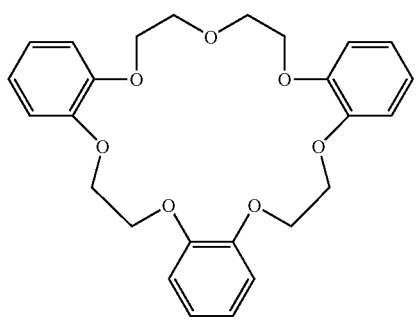
48

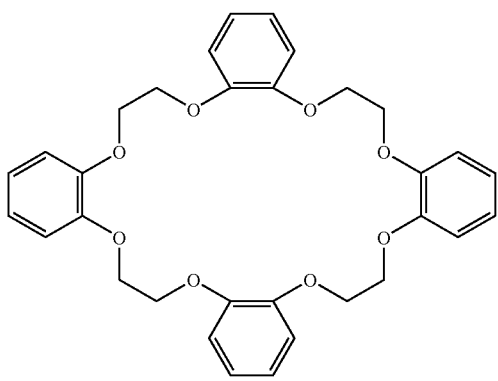
49

Preferably, R⁷ represents a group derived from benzo-18C6 crown ether of formula (IIIa):

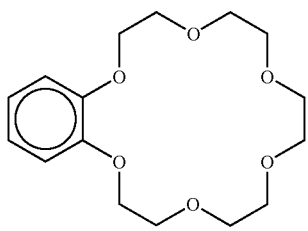
(IIIa)

or from 18C6 crown ether of formula (IIIb):

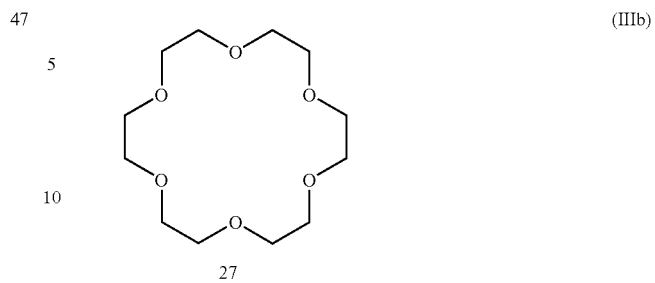
(IIIb)

The compounds of formula (I) can be prepared from the corresponding isocyanates of formula (IV):

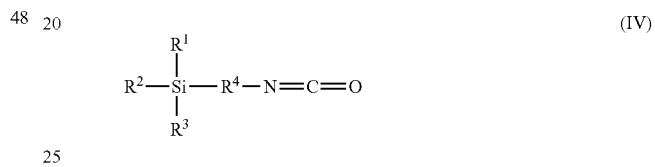
(IV)

in which $R^1$, $R^2$, $R^3$ and $R^4$ are as defined above, by reaction of the latter with an amine of formula $R^7$—$R^6$—$NH_2$ (V) or an alcohol of formula $R^7$—$R^6$—OH (VI) in which $R^7$ represents a group derived from a crown ether and $R^6$ has the meaning given above.

The reaction of an isocyanate of formula (IV) with an amine or an alcohol of formula (V) or (VI) is described, for example, in "Advanced Organic Chemistry", 4th edition, 1992, p. 891–903, published by John Wiley and Sons [6]. According to the invention, this reaction is carried out by mixing an isocyanate of formula (IV) with a compound of formula (V) or (VI) dissolved in a solvent which is nonreactive with respect to the isocyanate functional groups, such as halogenated hydrocarbons, for example chloroform and dichloromethane; ethers, such as diethylether, isopropylether, 1,4-dioxane or tetrahydrofuran; or hydrocarbons, such as alkanes (hexane, pentane, and the like) and benzene derivatives (benzene and derivatives, toluene, and the like).

The isocyanate of formula (IV) which is preferred in the invention is 3-(triethoxysilyl)propylisocyanate of formula (VII):

$(C_2H_5O)_3$ Si—$(CH_2)_3$—N=C=O  (VII)

which can be reacted with the amine of formula (VIIIa) or (VIIIb):

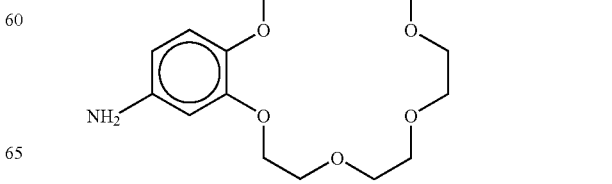
(VIIIa)

-continued

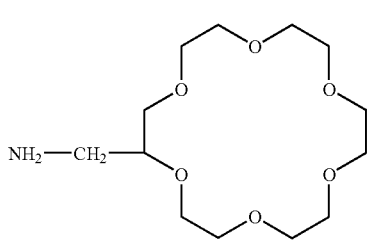
(VIIIb)

to produce the compound of formula (IXa) or (IXb):

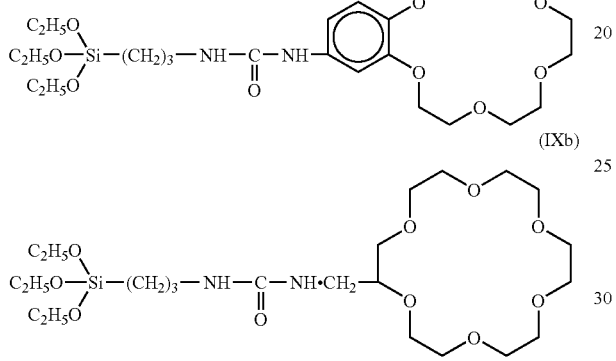

In this method of preparation of the compounds of formula (I) where $R^5$ represents NH, it is possible to proceed in the following way.

The amine of formula (V) is dissolved in an hydrous tetrahydrofuran (THF), for example in a proportion of 1 g of amine per 10 ml of THF, and then a stoichiometric amount of the isocyanate of formula (IV) is added to the solution. The reaction mixture is stirred at ambient temperature until the amine of formula (V) has completely disappeared, the latter being monitored by thin layer chromatography (Aldrich plates, silica gel on aluminium 219, B-29-1) using the chloroform-methanol (75:25) mixture as eluent.

The reaction mass is subsequently evaporated on a water bath at 30° C. under vacuum until the solvent has been completely removed. The yield is quantitative.

When it is desired to prepare compounds of formula (I) where $R^5$ represents O, the preparation is carried out in a similar way using an alcohol of formula (VI) instead of the amine of formula (V).

The isocyanates of formula (IV) used for the preparation of the compounds of formula (I) are commercial products or can be prepared by conventional processes known to a person skilled in the art.

The amines of formula (V) and the alcohols of formula (VI) are also commercial products or can be prepared by conventional processes.

Mention may be made, as examples of commercial products, of the following products:

2-(aminomethyl)-15-crown-5 (Aldrich Chemicals reference 38,841-6)

2-(aminomethyl)-18-crown-6 (Aldrich Chemicals reference 38,843-2)

4'-aminobenzo-15-crown-5 (Aldrich Chemicals reference 39,342-8)

4'-aminobenzo-18-crown-6 (Aldrich Chemicals reference 44,402-2)

4'-amino-5'-nitrobenzo-15-crown-5 (Aldrich Chemicals reference 44,403-0)

2-(hydroxymethyl)-12-crown-4 (Aldrich Chemicals reference 38,265-5)

2-(hydroxymethyl)-15-crown-5 (Aldrich Chemicals reference 38,842-4)

2-(hydroxymethyl)-18-crown-6 (Aldrich Chemicals reference 38,844-0)

This list is in no way limiting with regard to the compounds which can be used in the invention.

According to an alternative embodiment, the compounds of formula (I) in which $R^5$ represents NH or O can be prepared by reaction of an ethylene compound of formula (X):

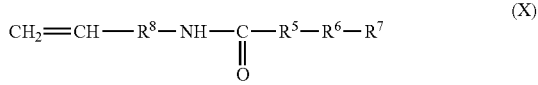
(X)

in which $R^5$, $R^6$ and $R^7$ are as defined above and $R^8$ represents a substituted or unsubstituted hydrocarbonaceous group of 1 to 18 carbon atoms optionally comprising, in its chain, one or more heteroatoms chosen from S, O, N and Si, with a compound of formula (XI):

(XI)

in which $R^1$, $R^2$ and $R^3$ are as defined above and $R^9$ is a single bond or a group of formula —$(CH_2)_t$—S— with t being an integer ranging from 1 to 9, $R^8$ and $R^9$ being such that the combination $R^9$—$(CH_2)_2$—$R^8$— corresponds to the $R^4$ group.

The ethylene compound of formula (X) can be prepared by reaction of a bifunctional isocyanate of formula (XII):

(XII)

where $R^8$ has the meaning given above, with an amine or an alcohol of formula (V) or (VI) described above. This reaction is identical to that described above for the preparation of the compounds of formula (I) by reaction of the isocyanate of formula (IV) with the amine or the alcohol of formula (V) or (VI). The ethylene compounds of formula (X) can thus be synthesized in the same way as the compounds of formula (I), the isocyanate of formula (IV) being replaced by the isocyanate of formula (XII).

The ethylene compounds of formula (XII) can be commercial products, such as allylisocyanate, or can be obtained by conventional processes, such as that disclosed in U.S. Pat. No. 4,518,758 [7].

The preferred compounds of formula (XII) are allylisocyanate, 4-allyloxyphenylisocyanate and 4-pentenyloxyphenylisocyanate.

The preferred compounds of formula (X) are as follows:

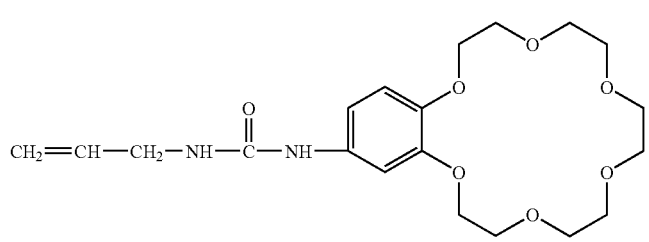

(Xa)

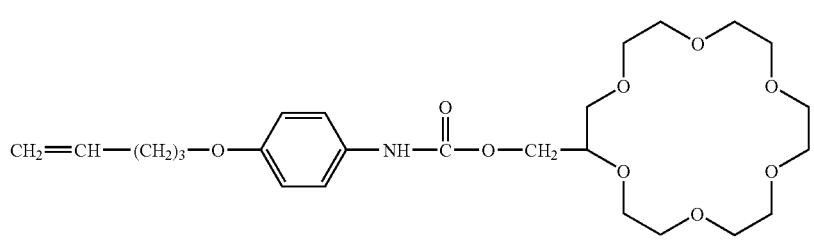

(Xb)

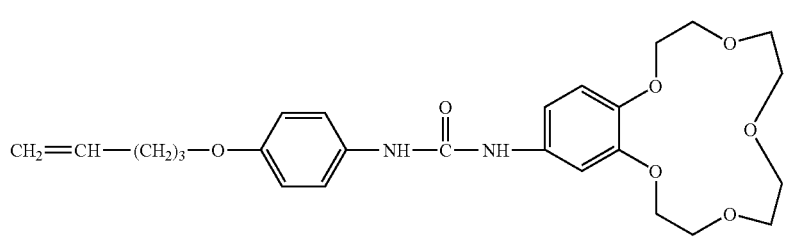

(Xc)

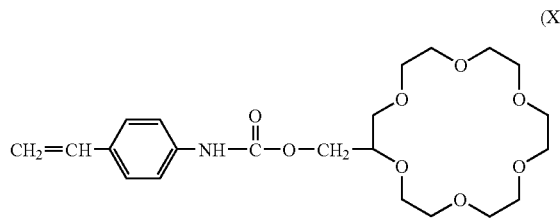

(Xd)

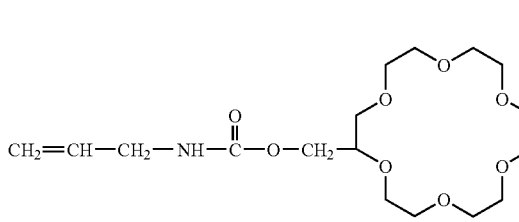

(Xe)

In this alternative form, when $R^9$ is a group of formula —$(CH_2)_t$—S—, use is made of the addition reaction of a silanethiol of formula (XI) with an ethylene compound of formula (X), which is an anti-Markonikov addition reaction resulting in the formation of thioethers, in the presence of free radicals.

A reaction of this type is described in the following documents: Tetrahedron Lett., 26, 1985, p. 3361–3364 [8] and New J. Chem., 13, 1989, p. 625–637 [9], for immobilizing compounds on a support via a covalent bond comprising a thioether functional group.

For this synthesis, the ethylene compound of formula (X) is first of all dissolved in an organic solvent which is inert with respect to thiol functional groups, for example toluene, tetrahydrofuran or chloroform, and then the silanethiol of formula (XI) in which $R^9$ represents —$(CH_2)_t$—S— is added, in a stoichiometric amount or in excess (up to 50 mol %), under cold conditions. A catalytic amount of a free radical initiator is added to the reaction medium. This initiator can be benzoyl peroxide. The reaction medium is brought to reflux until the starting ethylene compound of formula (X) has disappeared; this compound can be monitored by thin layer chromatography or by infrared spectrometry (disappearance of the absorption band of the ethylene functional groups). The preferred heating time is 24 h. The compound of formula (I) thus obtained is subsequently isolated by evaporating the solvent to dryness at normal pressure and then under vacuum.

The yield is quantitative (100%).

In this alternative form, the starting compounds of formula (XI) can be hydrosilanes ($R^9$ representing a single bond) or thiols ($R^9$ representing —$(CH_2)_t$—S—).

Mention may be made, as examples of such compounds, of trichlorosilane, trimethoxysilane, (3-mercaptopropyl)-trimethoxysilane and triethoxysilane, which are commercial compounds.

Other compounds of formula (XI) can be prepared by conventional processes.

This alternative form can be used in particular to prepare the compounds of formulae (XIIIa) and (XIIIb):

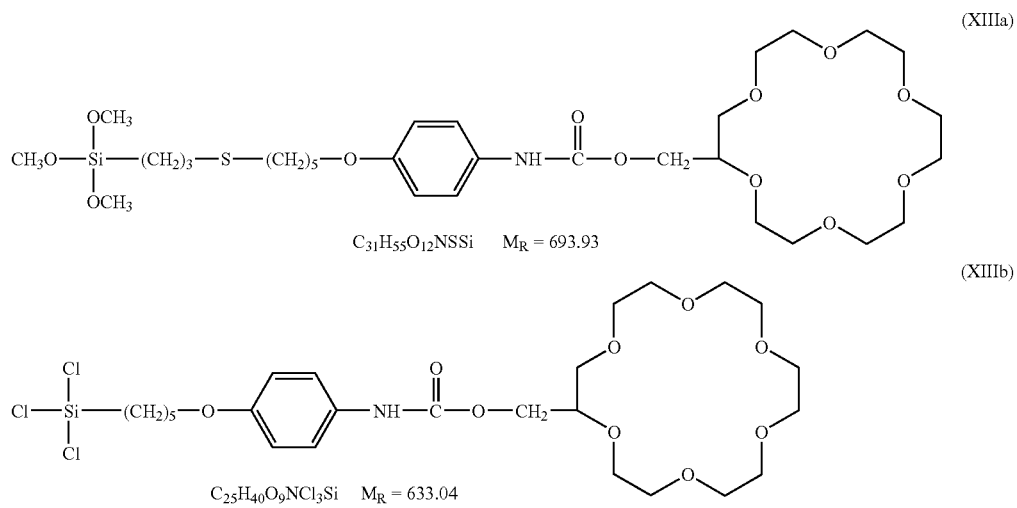

(XIIIa)

(XIIIb)

by reaction of the ethylene compound of formula (Xb):

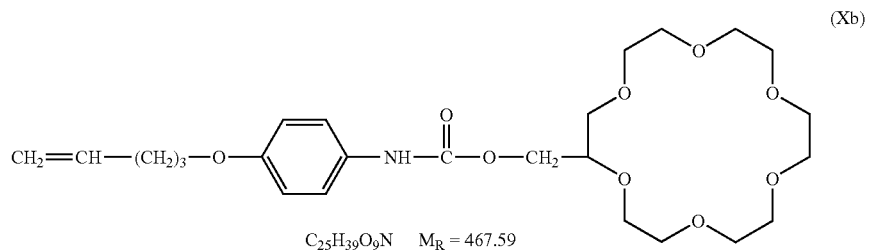

(Xb)

with the compound of formula (XVa) or (XVb):

 (XVa)

 (XVb)

In this alternative form, when $R^9$ is a single bond, the reaction of the ethylene compound of formula (X) with the hydrosilane of formula (XI) is a hydrosilylation reaction.

A reaction of this type is described in Chromatographia, Vol. 25, No. 4, 1988, pages 265–271 [10].

This reaction can be carried out in the following way.

The ethylene compound of formula (X) is dissolved in a solvent which is inert with respect to the hydrosilylation, for example an alkane, a benzene derivative or a halogenated hydrocarbon, in particular toluene, 1,4-dioxane or chloroform. The hydrosilane of formula (XI) is subsequently added to the solution, in a stoichiometric amount or in slight excess (up to 10 mol %), preferably in a stoichiometric amount, and a catalytic amount of a metal complex based on rhodium or on platinum, for example hexachloroplatinic acid, is added to the reaction medium. The reaction mass is brought to reflux of the solvent until the ethylene compound of formula (X) has disappeared and the hydrosilane of formula (XI) has disappeared. This disappearance can be monitored by thin layer chromatography or by infrared spectrometry (disappearance of the absorption band of the ethylene functional groups). The reaction medium is subsequently cooled and is then filtered to remove the rhodium- or platinum-based complex. The filtrate comprising the compound of formula (I) is brought to dryness. The yield is quantitative (100%).

The compounds of formula (I) of the invention can be used for the preparation of supports based on silica gel, of use in the chromatographic separation of metal cations and of organic molecules comprising amine functional groups.

Consequently, another subject-matter of the invention is a support based on silica gel, of use in the chromatographic separation of the isotopes of alkali metals or alkaline earth metals, comprising groups of formula (XVI):

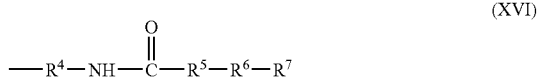

(XVI)

in which:

$R^4$ represents a substituted or unsubstituted hydrocarbonaceous group of 1 to 20 carbon atoms optionally comprising, in its chain, one or more heteroatoms chosen from S, O, N and Si;

$R^5$ represents —NH— or —O—;

$R^6$ represents a single bond or a substituted or unsubstituted hydrocarbonaceous group of 1 to 20 carbon atoms optionally comprising, in its chain, one or more heteroatoms chosen from S, O, N and Si; and $R^7$ represents a group derived from a crown ether, grafted to the silica gel by at least one covalent bond comprising at least one siloxane radical:

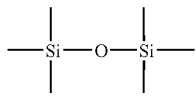

Preferably, the density of grafted groups of formula (XVI) is at least 0.5 mmol per g of support.

By way of example, the groups grafted to the silica gel correspond to one of the following formulae:

$R^1$, $R^2$ and $R^3$, which can be identical or different, represent a halogen atom or an alkoxy group of 1 or 2 carbon atoms;

$R^4$ represents a substituted or unsubstituted hydrocarbonaceous group of 1 to 20 carbon atoms optionally comprising, in its chain, one or more heteroatoms chosen from S, O, N and Si;

$R^5$ represents —NH— or —O—;

$R^6$ represents a single bond or a substituted or unsubstituted hydrocarbonaceous group of 1 to 20 carbon atoms optionally comprising, in its chain, one or more heteroatoms chosen from S, O, N and Si; and $R^7$ represents a group derived from a crown ether.

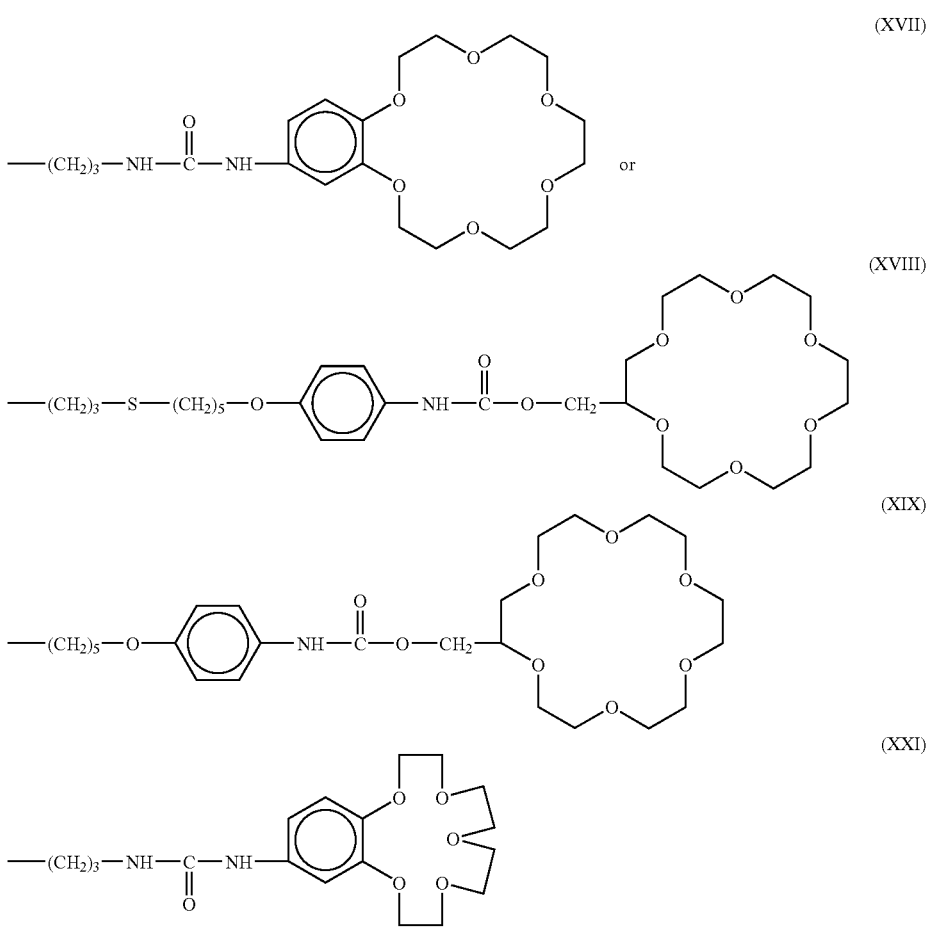

Such supports can be prepared by bringing a suspension of the silica gel in a liquid organic phase into contact with a solution in an organic solvent of a compound of formula (I):

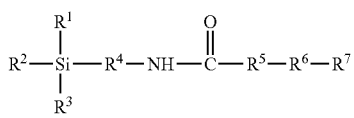

in which:

According to the invention, the liquid organic phase is composed of toluene, xylene, a pyridine/toluene mixture, a pyridine/xylene mixture, a pyridine/heptane mixture, a pyridine/xylene/water mixture, a pyridine/toluene/water mixture or a pyridine/heptane/water mixture.

Use is preferably made of a liquid organic phase comprising water.

This is because it has been found that, in the presence of water and despite the steric hindrance brought about by the volume of the cage of a crown ether, it is possible to obtain degrees of grafting, calculated from the results of microanalyses, which greatly exceed the maximum known to date and which can only be explained by a particularly effective "polymer graft". The notion of polymer graft was explained by Rosset, R., Claude, M. and Jardy, A. in the work "Chromatographies en phase liquide et supercritique" [Supercritical and liquid phase chromatographic methods], 3rd edition, 1991, published by Masson, 120 Boulevard Saint-Germain, 75280 Paris Cedex 06, pages 290 to 299 [11]. In particular, the polymerization reaction of trifunctional silanes in the presence of water with silica gel results in the formation of the following groups of formulae (XX) and (XXI):

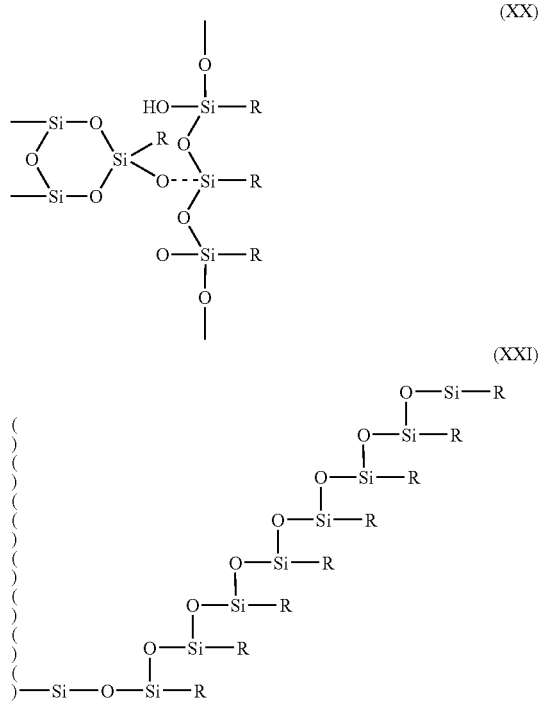

in which R represents the group of formula (XVI).

On page 293 of the document [11], it is indicated that a maximum level of carbon at 10% is obtained for a polymer graft based on octadecylsilane, corresponding to a mean grafting density of 1 to 2 µmol/m² (page 290, FIG. IX-6 of the same work). Surprisingly, the inventors observed that, on using a trifunctional silane in the presence of water and on carrying out the reaction for the silanization of the silica in a single stage, the levels of grafting obtained could greatly exceed 0.5 mmol of benzo-15C5 crown ether per gram of silica, which, depending on the characteristics of the crown ether and of the starting silica, made it possible to obtain levels of carbon (calculated by microanalysis) of much greater than 12%, and even up to 20% and more, and corresponding to levels of coverage of the order of 3.2 to 3.8 µmol of benzo-15C5 crown ether per m² of silica gel.

Methods for grafting silicon compounds to silica gel have been described in the work by Scott, R. P. W., "Silica Gel and Bonded Phases: Their Production, Properties and Use in LC", published by Wiley & Sons Ltd., 1993, pages 140–175 [12].

Toluene or xylenes, because of their high respective boiling points (110° C. and 138–140° C.), are recommended as reaction solvents for this grafting. The authors recommend drying the silica at 250° C. for 2 hours to remove the water present and then dispersing it (10 g in 100 ml of toluene) with toluene dried over sodium. A slight excess of silane with respect to stoichiometry, calculated with respect to the number of silanols present on the silica (these are generally given by the suppliers), is used. 5 ml of pyridine are necessary per 10 g of silica to dissolve the silane, the pyridine also being used to neutralize the hydrochloric acid released during the reaction. The pyridine/silane solution is run in under cold conditions onto the silica/toluene suspension over approximately 15' and then the reaction mass is brought to reflux for 5 hours. It is subsequently filtered and then the filter residue is washed sequentially with toluene, tetrahydrofuran, methanol, 50/50 (by volume) methanol/water and methanol, and then dried.

The same authors recommend a slightly different procedure if the silane employed is an alkoxysilane (and more generally a methoxy- or ethoxysilane). Pyridine is no longer used (as there is no longer HCl to trap) and the three starting materials (10 g of silica, 100 ml of toluene and a slight excess of alkoxysilane) are mixed and then brought to reflux for 5 hours with a reactor comprising a distillation column. The ethanol or the methanol formed during the silanization reaction is removed as it is formed by distillation at atmospheric pressure. The washing operations are subsequently carried out according to a procedure identical to that described for the use of a chlorosilane.

According to the invention, in order to obtain higher levels of grafting than are obtained with these methods, it is preferable to use, as silicon compound of formula (I), a trialkoxysilane ($R^1$, $R^2$ and $R^3$ being alkoxy groups) at high temperature, preferably using a liquid phase comprising variable proportions of pyridine and water. This is because the use of pyridine, which is a solvent with a basic nature, makes it possible, surprisingly and against all expectation, to promote the silanization reaction.

By way of example, the grafting can be carried out in a basic medium in the following way. 100 g of silica, for example having a specific surface of 300 m²/g, are suspended in a liquid phase composed of a xylene/pyridine/water mixture, for example 600 ml of xylene, 600 ml of pyridine and 9.72 g of water, i.e. 5.4 mmol of water per g of silica, and the combination is brought to 90° C. The compound of formula (I) is added thereto in a proportion, for example, of $180 \times 10^{-3}$ mol, i.e. 1.8 mmol, of crown ether-silane per g of silica. The reaction suspension is brought to gentle reflux for 24 h, then the reaction mass is filtered and the filter residue is washed and dried.

A grafting can also be carried out in an acidic medium, for example in a liquid 1,4-dioxane phase in the presence of hydrochloric acid, the grafting being carried out in the following way.

5 g of silica with a specific surface of 300 m²/g are suspended in 110 ml of 1,4-dioxane with 5.75 ml of 2.3N hydrochloric acid, and 9 mmol (i.e., 4.77 g of silane with a molar mass of 530.70) of silane of the general formula (I), in solution with 30 ml of 1,4-dioxane, are added, and the reaction suspension is brought to reflux for 24 hours. The suspension is cooled and then filtered, and the filter residue is washed and dried.

The supports based on silica gel of the invention are particularly of use in the separation by chromatography of cations or of molecules comprising amine functional groups.

In this case, the amine functional groups of the molecules are complexed by an inorganic or organic acid, for example perchloric acid, and the mechanism of separation involves different complexing constants of the $NH_3^+$ ammonium functional groups for each amino acid.

The $R^7$ group derived from crown ether is chosen, of course, according to the cations or molecules to be separated.

The chromatographic separation can be carried out by high performance liquid chromatography according to the rules normally used for this technique.

Other characteristics and advantages of the invention will become more clearly apparent on reading the description which follows, given, of course, by way of illustration and without implied limitation, of implementational examples in accordance with the invention, with reference to the appended drawings.

DETAILED ACCOUNT OF IMPLEMENTATIONAL EXAMPLES

EXAMPLE 1

Figure 1:
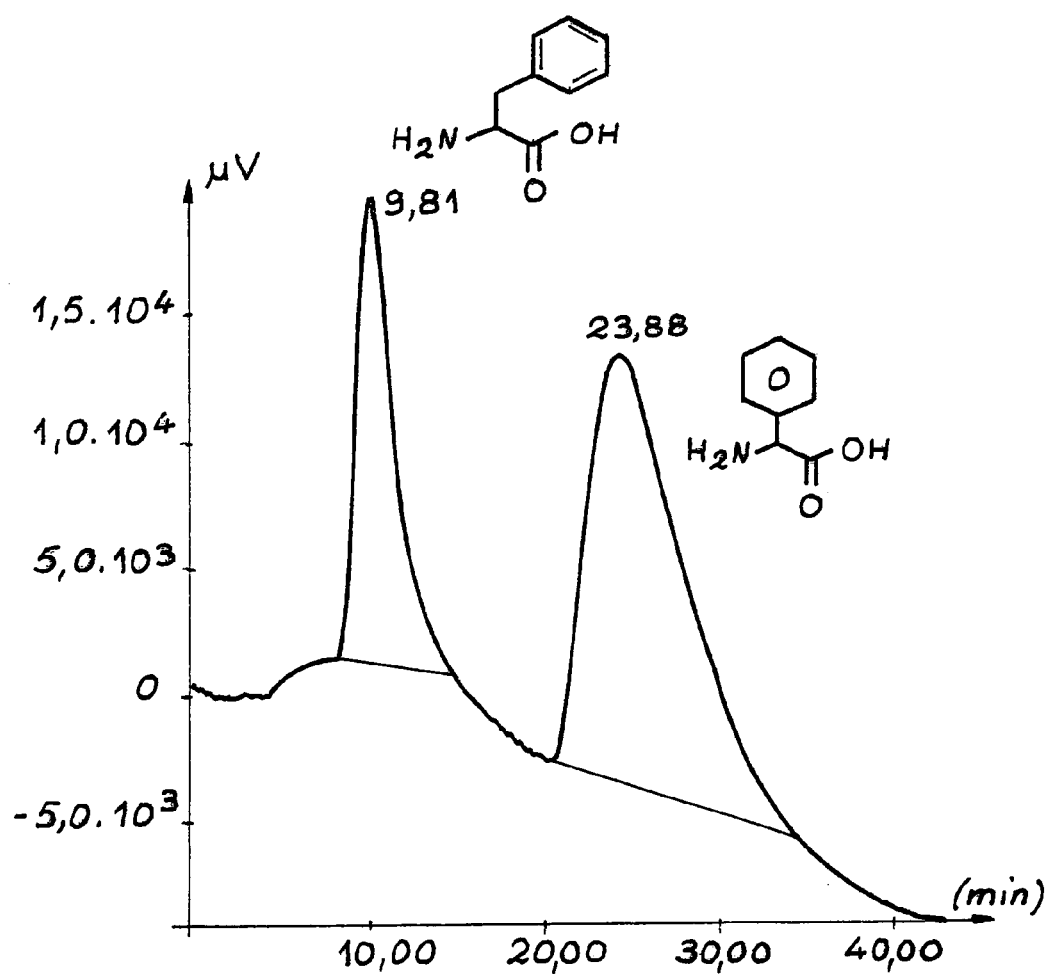
FIGS. 1 and 2 are chromatograms illustrating the separation of the following amino acids:
phenylalanine/phenylglycine (FIG. 1)
phenylalanine/phenylalanine ethyl ester (FIG. 2).

Synthesis of 4-[3-(triethoxysilyl)propyl]-ureido-benzo-18-crown-6 of formula (IXa)

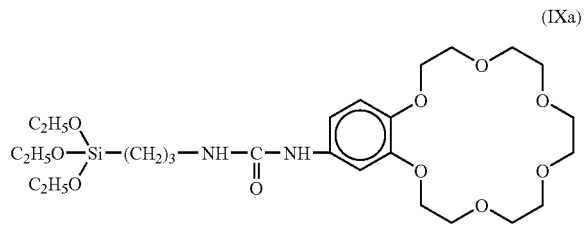

31.43 g of 97% 4'-aminobenzo-18-crown-6 (Aldrich reference 44,402-2, $M_R$=327.38), i.e. 96 mmol, are dissolved in 460 ml of methylene chloride. 26.12 g of 3-(triethoxysilyl)propylisocyanate (Aldrich reference 41,336-4, $M_R$=247.37), i.e. 105.6 mmol, corresponding to 10% excess with respect to the crown ether, are added and the reaction medium is stirred at ambient temperature for 48 hours. The solution is subsequently brought to dryness by evaporation on a water bath at 40° C. under vacuum to a constant weight. 58 g of the compound (IXa) are obtained. The yield is greater than 100% as the silane is used in excess.

EXAMPLE 2

Synthesis of 4-(3-trimethoxysilyl-propylthiopenty-loxy)phenylcarbamatomethyl-18-crown-6 of formula (XIIIa)

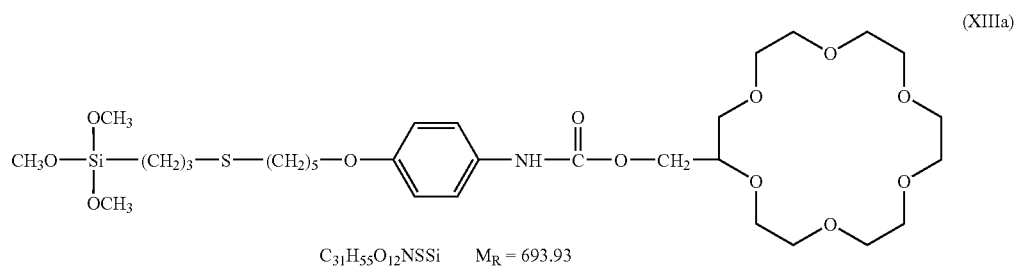

1) Synthesis of 4-(pent-4-enoxy)phenylisocyanate of formula (XXII)

a) Preparation of para-(pent-4-enoxy)benzoic acid 2 g of sodium hydroxide, 15 ml of distilled water, 7.6 g of methyl 4-hydroxybenzoate, 0.16 g of tetrabutylammonium bromide and 5.92 ml of 5-bromopent-1-ene are successively placed in a reactor. Vigorous stirring is maintained at ambient temperature for 12 hours. After having added 30 ml of a 2.5M sodium hydroxide solution, the reaction medium is heated at 60–80° C. for 90 minutes. It is subsequently diluted with 120 ml of distilled water and extracted with two times 50 ml of diethylether. The aqueous phase is acidified with 10 ml of concentrated hydrochloric acid in order to make possible the precipitation of the acid. After filtration, washing with distilled water and then drying in a desiccator over $P_2O_5$, the acid is obtained with a yield of 93%.

b) Preparation of the acid chloride of para-(pent-4-enoxy)benzoic acid 10.3 g of para-(pent-4-enoxy)benzoic acid are suspended in 60 ml of toluene to which 17 ml of thionyl chloride are added. The reaction mixture is heated at reflux for 30 minutes and is then evaporated under vacuum. The residue obtained is distilled under vacuum (110° C./1 mm of Hg). The yield of this synthesis is 85%.

c) Preparation of para-(pent-4-enoxy)benzoylazide

A solution of 11.27 g of para-(pent-4-enoxy)benzoyl chloride dissolved in 15 ml of acetone is added dropwise at ambient temperature to an aqueous solution of sodium azide (3.9 g in 22 ml of distilled water) while maintaining vigorous stirring. At the end of the addition, the reaction medium is stirred for one hour and then diluted with 50 ml of water. After separation by settling, the colourless oil obtained is dried over magnesium sulphate (yield=80%).

d) Preparation of
para-(pent-4-enoxy)phenylisocyanate 11.6 g of para-(pent-4-enoxy)benzoylazide are dissolved in 80 ml of anhydrous toluene and then brought to reflux for 90 minutes. The solvent is subsequently evaporated under vacuum and the residue, which is present in the form of a colourless oil, is distilled under vacuum (100° C./1 mm of Hg). The yield of this synthesis is 94%.

2) Synthesis of 2-[4-(pent-4-enoxy)phenylcarbamatomethyl]-18-crown-6 of formula (Xb)

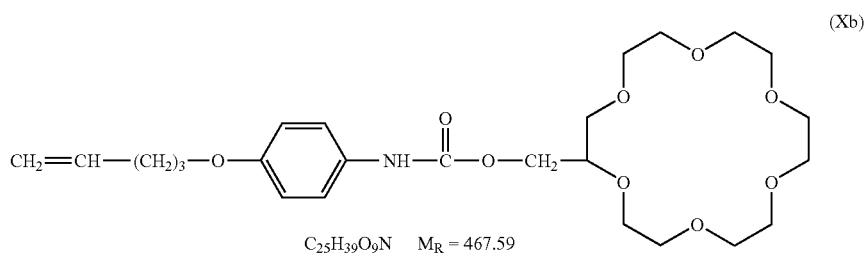

$C_{25}H_{39}O_9N$    $M_R = 467.59$ 8.13 g of compound (XXII) synthesized above, i.e. 40 mmol, are dissolved in 80 ml of anhydrous tetrahydrofuran. 40 mmol of 2-(hydroxymethyl)-18-crown-6 (Aldrich reference 38 440-0, $C_{13}H_{26}O_7$, $M_R$=294.35), i.e. 11.77 g, dissolved beforehand in 110 ml of tetrahydrofuran, are added and the reaction mas stirred at between 20 and 30° C. for 48 hours. The medium is subsequently brought to dryness by evaporation under vacuum on a water bath at 40° C. to constant weight. The yield is quantitative. 20 g of compound (Xb) are obtained. It is used as is in the following stage.

3) Anti-Markonikov addition of the silanethiol

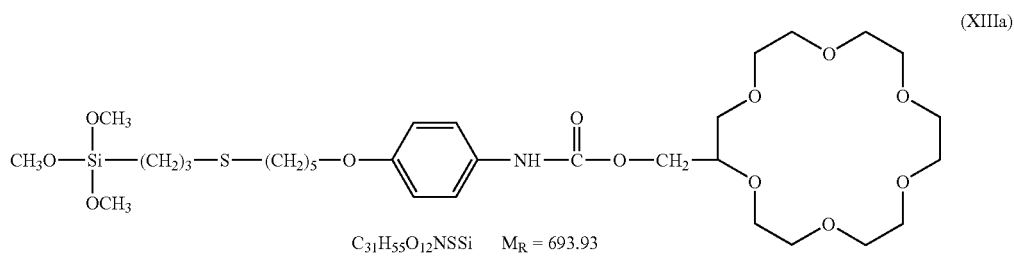

$C_{31}H_{55}O_{12}NSSi$    $M_R = 693.93$ 20 g or 40 mmol of compound (Xb) synthesized in 2-2 are dissolved in 20 ml of chloroform. 7.85 g (40 mmol) of (3-mercaptopropyl)trimethoxysilane (Aldrich reference 13,561-7, $C_6H_{16}O_3SSi$, $M_R$=196.34), dissolved beforehand in 30 ml of chloroform, are added and the solution is brought to reflux for 5 days. 20 mg of benzoyl peroxide are added approximately every 20 hours. The reaction medium is subsequently brought to dryness by evaporation under vacuum to a constant weight. The yield is quantitative. 29 g of compound (XIIIa) are obtained.

EXAMPLE 3

Synthesis of 2-[4-(5-(trichlorosilyl)pentyloxy)phenylcarbamatomethyl]-18-crown-6 of formula (XIIIb)

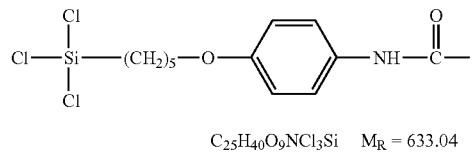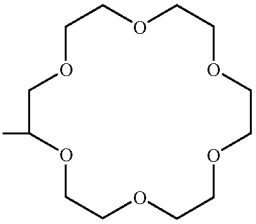

$C_{25}H_{40}O_9NCl_3Si$    $M_R = 633.04$ 49.8 g of compound (Xb) (synthesized in Example 2—2) (100 mmol) are dissolved in 200 ml of anhydrous dimethylformamide, dried beforehand over sodium. 13.54 g of trichlorosilane (Aldrich, reference 17,555-2, $SiHCl_3$, $M_R=135.45$), i.e. 100 mmol, dissolved beforehand in 50 ml of anhydrous DMF dried over sodium, are added to the preceding solution. 0.4 g (1 mmol) of hexachloroplatinic acid hydrated with 1 $H_2O$ (or hydrogen hexachloroplatinate (IV) hydrate, Aldrich catalogue 25,409-2, $M_R=409.82$, $H_2PtCl_6.1H_2O$) is added to the reaction mass, which is brought to 80° C. under an argon atmosphere for 60 hours. 0.4 g of hexachloroplatinic acid is added after 20 hours and 40 hours. The medium is cooled and then filtered through a sintered glass funnel No. 3 under argon.

The disappearance of the ethylene double bonds carried by the starting compound (Xb) (synthesized in Example 2-2) is monitored by infrared spectrometry.

The filtrate is maintained under argon with the exclusion of air and moisture. 63.30 g, 100 mmol, of compound (XIIIb) are obtained.

The following Examples 4, 5 and 6 illustrate the preparation of supports based on silica gel which are grafted by compound (IXa), compound (XIIIa) and compound (XIIIb).

EXAMPLE 4

Preparation of a Support Based on Silica Gel Grafted by Compound (IXa)

5 g of silica gel (spherical particles with a diameter of 40 to 63 μm, with a specific surface of 300 m²/g and with a pore diameter of 120 Å), treated beforehand with hydrochloric acid at reflux, are suspended in 50 ml of 1,4-dioxane. 9 mmol (corresponding to 1.8 mmol of compound (IXa)/g of silica), i.e. 5.44 g, of compound (IXa) synthesized in Example 1, dissolved beforehand in 50 ml of 1,4-dioxane, are added to the silica gel suspension. 5.4 mmol of water per gram of silica, or 27 mmol, i.e. 486 μl, are added to the reaction mass, along with 1 ml of HCl, i.e. 12 mmol, or 2.4 mmol per gram of silica. The reaction suspension is brought to reflux for 48 hours. It is subsequently cooled and then filtered through a sintered glass funnel No. 3. The precipitate is washed with 100 ml of methanol, 100 ml of triethylamine, 100 ml of water and then 2 times 100 ml of acetone. The precipitate is dried at 8° C. in an oven under vacuum to a constant weight.

7.19 g of silica gel (dry weight) are obtained.

The increase in weight ΔM is 0.77 g.

The % of carbon by elemental microanalysis is 15.25%, i.e. 0.71 mmol of compound (IXa) per g of silica.

EXAMPLE 5

Preparation of a Support Based on Silica Gel Grafted by Compound (XIIIa)

40 g of silica gel (spherical particles with a diameter of 20 to 40 μm, with a specific surface of 300 m²/g and with a pore diameter of 120 Å), treated beforehand with hydrochloric acid or with nitric acid at reflux, are suspended in a pyridine/heptane 235 ml/32.5 ml mixture. The suspension is subsequently brought to reflux of the pyridine/heptane/water ternary azeotrope and 100 ml of condensate are distilled using a column equipped with a reflux head and with a fractionation system. 50 g (72 mmol, or 1.8 mmol of compound (XIIIa) per g of silica) of compound (XIIIa) of Example 2, dissolved beforehand in 300 ml of toluene, are added to the reaction suspension. The reaction mass is brought to reflux for 48 hours while distilling 150 ml of condensate. 3.9 g of water (i.e. 5.4 mmol of water/g of silica) are added to the reaction mass after cooling to approximately 90–95° C. The reaction medium is stirred at 90–95° C. for an additional 48 hours. It is subsequently cooled and then filtered through a sintered glass funnel No. 3. The insoluble material is washed with 300 ml of methanol, then with 300 ml of water and then with two times 200 ml of acetone. It is subsequently brought to dryness at 80° C. under vacuum in an oven.

80.0 g of silica gel (dry weight) are obtained. The increase in weight is 40.0 g. The percentage of carbon by elemental microanalysis is 26.54%. The amount in mmol of compound (XIIIa) per g of support is 0.79 mmol/g (calculated by microanalysis).

EXAMPLE 6

Preparation of a Support Based on Silica Gel Grafted by Compound (XIIIb)

The filtrate obtained in Example 3 is stirred and then 55.5 g of silica gel (spherical particles with a diameter of 5 μm, specific surface of 300 m²/g and pore diameter of 120 Å) are added (1.8 mmol of compound (XIIIb)/g of silica). 100 ml of pyridine are added. The reaction mass is brought to reflux for 48 hours. 2.4 mmol of water/g of silica, i.e. 2.4 g, are added to the mass and reflux is again maintained for 48 hours. The reaction medium is filtered through a sintered glass funnel No. 3 and then washed with 500 ml of methanol, 500 ml of water and then two times 500 ml of acetone. The solid is dried at 80° C. under vacuum to constant weight.

102 g of silica gel (dry weight) are obtained.

The increase in weight is 46.5 g.

The % of carbon by microanalysis is 26.08%.
The level of grafting by microanalysis is 0.87 mmol/g.

EXAMPLES 7 TO 12

Preparation of Supports Based on Silica Gel Grafted by aminobenzo-15C5 Crown Ether In these examples, the same procedure is followed as in Example 4 but the amounts of silica gel and of compound (XX), 4-[3-(trimethoxysilyl)propyl]ureidobenzo-15-crown-5 of formula:

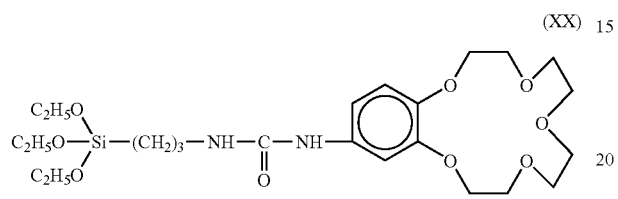
(XX)

and the solvents given in Table 1 are used.

Compound (XX) is obtained in the following way:

27.2 g of 97% 4'-aminobenzo-15-crown-5 (Aldrich reference 39,342-8, $M_R$=283.33), i.e. 96 mmol, are dissolved in 345 ml of chloroform. 26.12 g of 3-(triethoxysilyl)propyl-isocyanate (Aldrich reference 41,336-4, $M_R$=247.37), i.e. 105.6 mmol, corresponding to 10% excess with respect to the crown ether, are added and the reaction medium is stirred at ambient temperature for 48 hours. The yellow solution obtained is brought to dryness by evaporation on a water bath at 40° C. under vacuum to constant weight. 53.32 g of compound (XX) are obtained. The yield is greater than 100% as the silane is used in excess.

The results obtained for the preparation of the supports, i.e. the increase in weight, the % of carbon by elemental microanalysis and the amount of grafted compound (in mmol/g of silica) are also given in Table 1.

In Examples 7 to 12, the levels of grafting, expressed as mmol of grafted compound per g of silica and calculated from the contents of carbon obtained by elemental microanalysis, were obtained according to the calculation method indicated by Rosset R. in the reference [11], page 281.

EXAMPLE 13

Separation of Amino Acids

The support obtained in Example 6 (silica gel grafted by compound (XIIIa)) is used to separate phenylalanine and phenylglycine by high performance liquid chromatography (HPLC). The separation is carried out in the following way.

3 grams of the support of Example 6 are suspended in 20 ml of ethanol and are used to fill an HPLC column with internal dimensions of 250×4.6 mm.

The column is subsequently rinsed with 100 ml of ethanol and then 100 ml of water. It is subsequently conditioned in the following mobile phase: water +$10^{-3}$M perchloric acid for 3 hours. Separation is carried out in this mobile phase under isocratic conditions. The pressure is 8.1 MPa. The mixture to be separated is phenylalanine/phenylglycine (30/70% by weight), two amino acids with a similar chemical structure and which differ only in a methylene group.

The flow rate is set at 1 ml/min. UV detection is carried out at 254 nm. The O.D. (optical density) scale is 0.5. The integration system used is a microcomputer equipped with Unipoint (Gilson) integration software. The results are given in Table 2.

TABLE 2

| Compound | Retention time (min) | % Area | Selectivity factor α |
|---|---|---|---|
| Phenylalanine | 9.81 | 29.9 | |
| Phenylglycine | 23.88 | 70.1 | 3.07 |

10 µl of a 1% solution in the mobile phase are injected. The chromatogram is reproduced in FIG. 1.

EXAMPLE 14

Separation of Amino Acids

The same procedure as in Example 13 is followed except for the flow rate, which is set at 2 ml/min, in order to separate a mixture of phenylalanine/phenylalanine ethyl ester (35/65% by weight).

The results are given in Table 3.

TABLE 3

| Compound | Retention time (min) | % Area | Selectivity factor α |
|---|---|---|---|
| Phenylalanine | 4.50 | 36 | |
| Phenylalanine ethyl ester | 9.49 | 64 | 2.66 |

Figure 2:
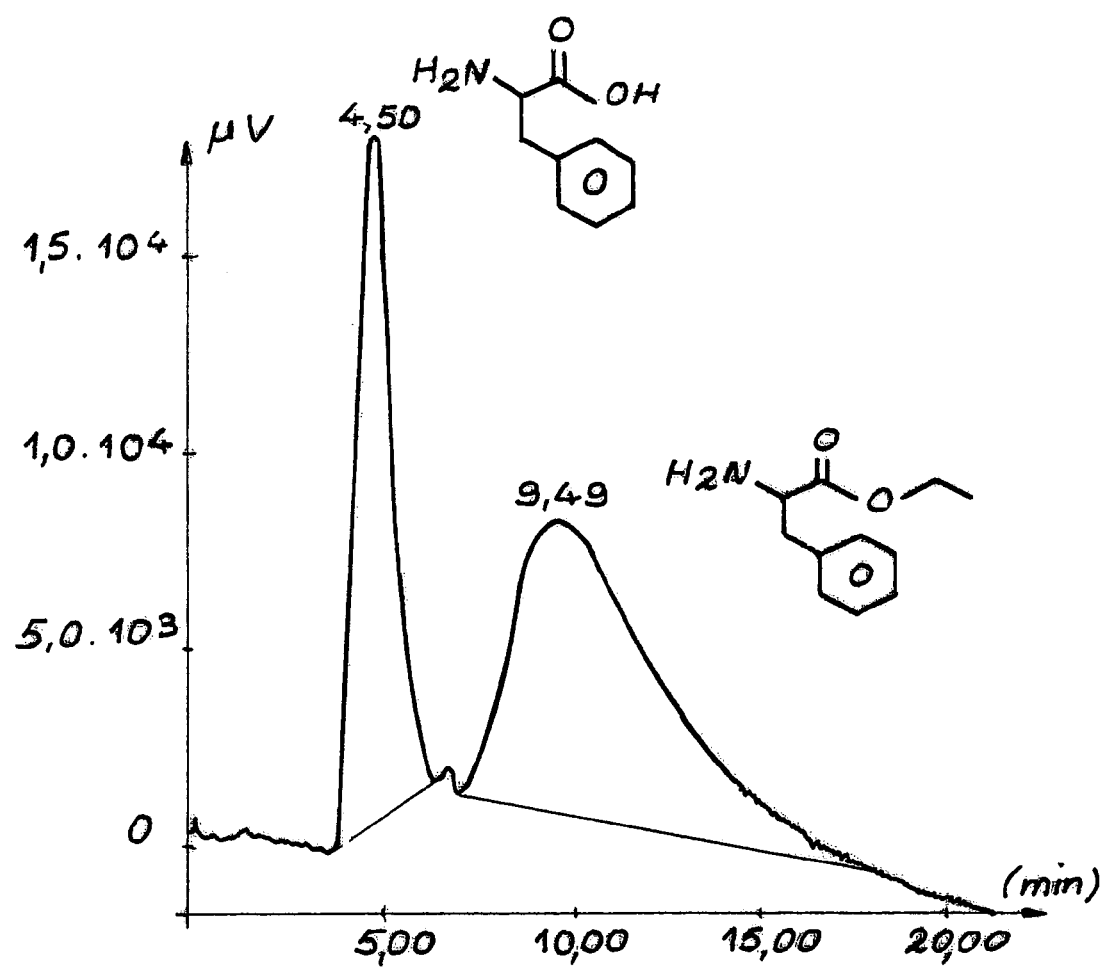

The chromatogram obtained is illustrated in FIG. 2.

The results of Examples 13 and 14 show that the support of Example 6 in accordance with the invention makes it possible to obtain satisfactory separation of amino acids.

EXAMPLE 15

Separation of Cations 3 grams of the support of Example 7 are suspended in 20 ml of ethanol and are used to fill an HPLC column with internal dimensions of 250×4.6 mm by the "wet route" method under 70 MPa (700 bar) of pressure. The column is rinsed with 100 ml of water and then 100 ml of ethanol. An elution gradient is produced over 30' from 100% anhydrous ethanol to 100% water after injection. The injection conditions are as follows: 20 µl of a 1% solution of LiCl+NaCl (66/34% by weight) in water. Detection is carried out using an evaporative light scattering detector (ELSD Sedex 45 from SEDERE-Alfortville—France), the conditions being as follows: air pressure over the detector 0.22 MPa (2.2 bar), evaporation temperature 50° C., flow rate 1 ml/min.

Figure 3:
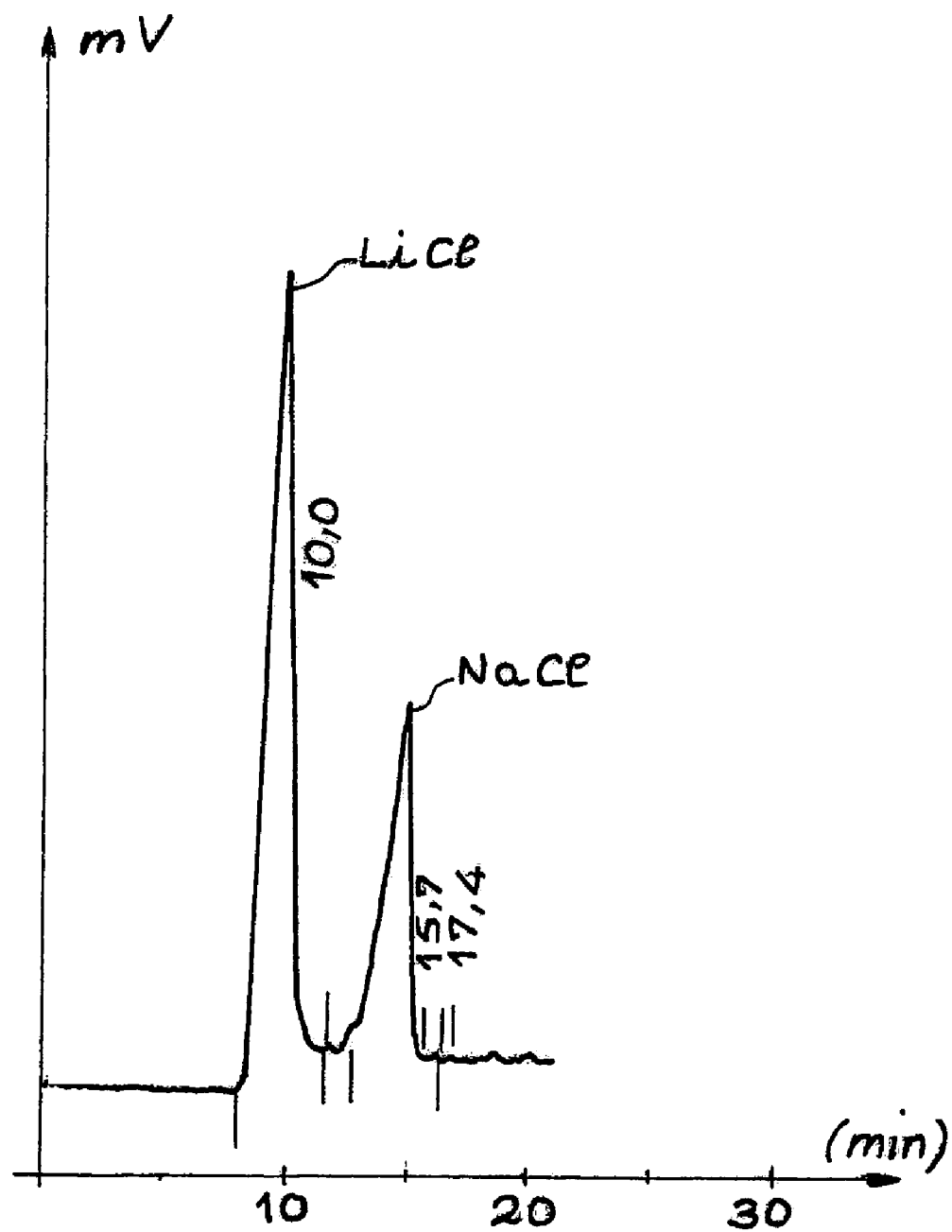
FIG. 3 is a chromatogram illustrating the separation of the Li and Na cations.

The chromatogram obtained is reproduced in FIG. 3 with the raw integration data (Spectrophysics SP4290 integrator):

| Compound | Retention time $T_R$ (minutes) | % Area | Capacity factor k' | Selectivity α $T_{R2}/T_{R1}$ |
|---|---|---|---|---|
| LiCl | 10.0 | 66.02 | 2.33 | |
| NaCl | 15.7 | 33.98 | 4.23 | 1.81 |

The zero retention time To was determined by injection of a sodium azide solution. It is 3.0 min on average. The capacity factor k' is determined experimentally by the relationship:

$$k' = \frac{T_R - T_0}{T_0}.$$

TABLE 1

| Ex. | Weight of silica (g) | mmol of compound (XX) per g of silica | Solvent | ΔM increase in weight (g) | mmol of grafted compound (I)/g of silica (calculated with regard to ΔM) | % of C (elemental microanalysis) | mmol of grafted compound (I) per g of silica (calculated with regard to % C from microanalysis) |
|---|---|---|---|---|---|---|---|
| 7 | 5 | 1.2 | toluene | 0.8 | 0.36 | 11.40 | 0.50 |
| 8 | 5 | 1.2 | xylene | 1.0 | 0.46 | 11.49 | 0.55 |
| 9 | 100 | 1.2 | pyridine/toluene | 21.92 | 0.5 | 11.22 | 0.51 |
| 10 | 100 | 1.8 | pyridine/xylene | 30.34 | 0.69 | 15.08 | 0.70 |
| 11 | 40 | 1.8 | pyridine/xylene/water | 15.32 | 0.87 | 17.05 | 0.79 |
| 12 | 5 | 1.8 | 1,4-dioxane/HCl | 2.19 | 0.77 | 15.25 | 0.71 |

REFERENCES CITED

[1] J. Am. Chem. Soc., 97, 1975, p. 1259–1261
[2] Anal. Chem., 55, 1983, p. 463–467
[3] Bull. Chem. Soc. Jpn, 56, 1983, p. 3052–3056
[4] Bull. Chem. Soc. Jpn, 59, 1986, p. 1475–1480
[5] Anal. Chem., 68, 1996, p. 2811–2817
[6] "Advanced Organic Chemistry", 4th edition, 1992, p. 891–903, published by John Wiley and Sons
[7] U.S. Pat. No. 4,518,758
[8] Tetrahedron Lett., 26, 1985, p. 3361–3364
[9] New J. Chem., 13, 1989, p. 625–637
[10] Chromatographia, Vol. 25, No. 4, 1988, pages 265–271
[11] Rosset, R., Claude, M. and Jardy, A. in the work "Chromatographies en phase liquide et supercritique" [Supercritical and liquid phase chromatographic methods], 3rd edition, 1991, published by Masson, 120 Boulevard Saint-Germain, 75280 Paris Cedex 6, pages 290 to 299
[12] Scott, R. P. W., "Silica Gel and Bonded Phases: Their Production, Properties and Use in LC", published by Wiley & Sons Ltd., 1993, pages 140–175

The invention claimed is:

1. A compound of formula (I):

$$R^2-\underset{\underset{R^3}{|}}{\overset{\overset{R^1}{|}}{Si}}-R^4-NH-\overset{\overset{O}{\|}}{C}-R^5-R^6-R^7 \qquad (I)$$

wherein:

$R^1$, $R^2$ and $R^3$, which can be identical or different, represent a halogen atom or an alkoxy group of 1 or 2 carbon atoms;

$R^4$ represents a substituted or unsubstituted sequence of alkylene and arylene groups of 1 to 20 carbon atoms connected by O, S, N and/or Si atoms;

$R^5$ represents —NH— or —O—;

$R^6$ represents a single bond or a substituted or unsubstituted alkylene group of 1 to 20 carbon atoms; and $R^7$ represents a benzo-18C6 or 18C6 crown ether.

2. The compound according to claim 1, wherein $R^1$, $R^2$ and $R^3$ represent the methoxy group or the ethoxy group.

3. The compound according to claim 1, wherein $R^1$, $R^2$ and $R^3$ represent chlorine.

4. The compound according to claim 1, wherein $R^4$ represents a substituted or unsubstituted sequence of alkylene and arylene groups of 1 to 20 carbon atoms connected by O and/or S atoms.

5. The compound according to claim 4, wherein $R^4$ is a group of formula (II):

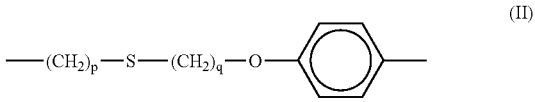

in which p and q are identical or different integers such that $p+q \leq 14$.

6. The compound according to claim 1, wherein $R^6$ is a single bond or a methylene group.

7. A compound selected from the group consisting of:

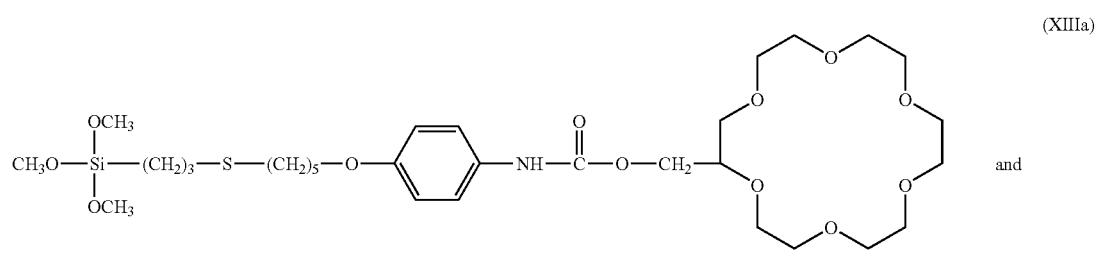

-continued

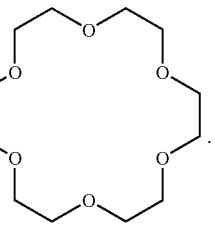
(XIIIb)

8. A process for the preparation of a compound of formula (I):

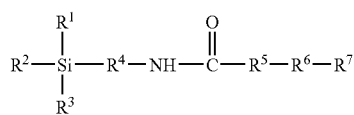
(I)

wherein:

R$^1$, R$^2$ and R$^3$, which can be identical or different, represent a halogen atom or an alkoxy group of 1 or 2 carbon atoms;

R$^4$ represents a substituted or unsubstituted sequence of alkylene and arylene groups of 1 to 20 carbon atoms connected by O, S, N and/or Si atoms;

R$^5$ represents —NH— or —O—;

R$^6$ represents a single bond or a substituted or unsubstituted alkylene group of 1 to 20 carbon atoms; and R$^7$ represents a benzo-18C6 or 18C6 crown ether comprising reacting a compound of formula (X):

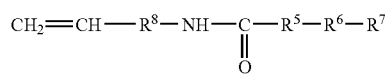
(X)

in which R$^5$, R$^6$ and R$^7$ are as defined in formula (I) and R$^8$ represents a substituted or unsubstituted sequence of alkylene and arylene groups of 1 to 18 carbon atoms connected by O, S, N and/or Si atoms, with a compound of formula (XI):

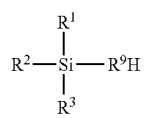
(XI)

in which R$^1$, R$^2$, and R$^3$ are as defined in formula (I) and R$^9$ is a single bond or a group of formula —(CH$_2$)$_t$—S— with t being an integer from 1 to 9, R$^8$ and R$^9$ being such that the combination R$^9$—(CH$_2$)$_2$—R$^8$— corresponds to the R$^4$ group.

9. The process according to claim 8 for the preparation of the compound of formula (XIIIa):

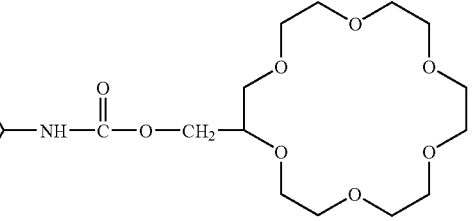
(XIIIa)

wherein the compound of formula (Xb):

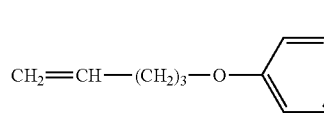
(Xb)

is reacted with the compound of formula (XVa):
(CH$_3$O)$_3$—Si—(CH$_2$)$_3$—SH.
10. The process according to claim 8 for the preparation of the compound of formula (XIIIb):
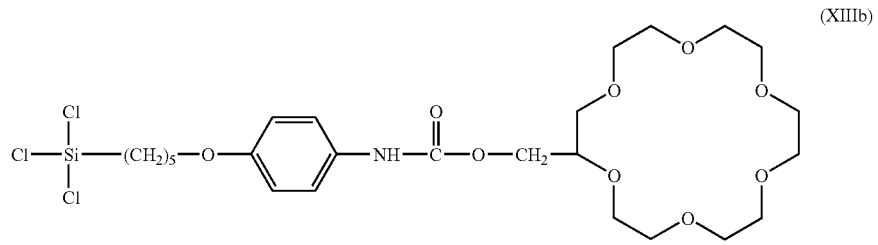
wherein the compound of formula (Xb):
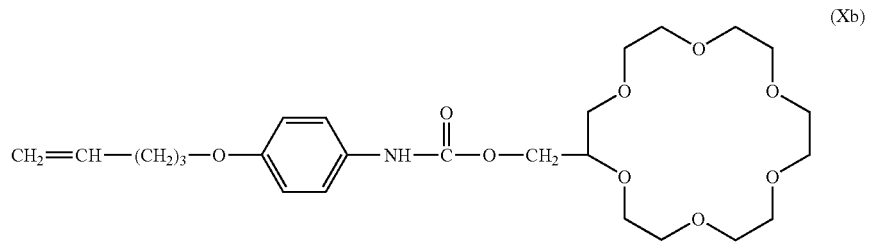
is reacted with the compound of formula Cl$_3$SiH (XVb).
* * * * *

UNITED STATES PATENT AND TRADEMARK OFFICE
CERTIFICATE OF CORRECTION

| | | |
|---|---|---|
| PATENT NO. | : 7,230,123 B2 | Page 1 of 1 |
| APPLICATION NO. | : 10/502120 | |
| DATED | : June 12, 2007 | |
| INVENTOR(S) | : Yves Barre et al. | |

It is certified that error appears in the above-identified patent and that said Letters Patent is hereby corrected as shown below:

On The Title Page, Item (73):

The Assignee should be changed from "Commissariat a l'Energir Atomique" to read --Commissariat a l'Energie Atomique--.

Column 29, lines 6 and 11 Formula XIIIb, both portions of the formula reading "$OCH_3$" should read --Cl--.

Column 30, line 33, that portion of the formula reading "$_1$-S-" should read --$_t$-S- --.

Signed and Sealed this

Sixth Day of November, 2007

JON W. DUDAS
*Director of the United States Patent and Trademark Office*